United States Patent [19]

Bopp

[11] Patent Number: 5,009,999

[45] Date of Patent: Apr. 23, 1991

[54] METHOD FOR BIODEGRADING PCBS

[75] Inventor: Lawrence H. Bopp, Scotia, N.Y.

[73] Assignee: General Electric Company, Schenectady, N.Y.

[21] Appl. No.: 325,739

[22] Filed: Mar. 20, 1989

Related U.S. Application Data

[62] Division of Ser. No. 866,501, May 23, 1986, Pat. No. 4,843,009.

[51] Int. Cl.$^5$ .................. C12Q 1/02; C10G 17/00; C10G 45/00
[52] U.S. Cl. .................................. 435/29; 208/262.5
[58] Field of Search ................ 435/29; 208/262.5

[56] References Cited

U.S. PATENT DOCUMENTS 4,843,009 6/1989 Bopp .................. 435/253.3

Primary Examiner—Robert A. Wax
Assistant Examiner—Bradley L. Sisson
Attorney, Agent, or Firm—William A. Teoli; James C. Davis, Jr.; William H. Pittman

[57] ABSTRACT

An aerobic biodegradation method is provided utilizing a biologically pure culture of a strain of *Pseudomonas putida* which is capable of degrading PCBs free of vicinal hydrogen atoms as well as congeners unchlorinated in either a 2,3 position, a 3,4 position, or both 2,3 or 3,4 positions.

9 Claims, No Drawings

METHOD FOR BIODEGRADING PCBS

This application is a division of application Ser. No. 866,501, filed May 23, 1986, now U.S. Pat. No. 4,843,009.

BACKGROUND OF THE INVENTION

Prior to the present invention, various techniques were developed for eliminating PCBs, or polychlorinated biphenyls from the environment. In instances where the PCBs were dissolved in an organic solvent, such as transformer oil, the contaminated solution could be treated with a mixture of polyethylene glycol and alkali metal hydroxide as shown by Brunelle, U.S. Pat. No. 4,351,718, assigned to the same assignee as the present invention and incorporated herein by reference. In many cases, the PCBs are located in more exposed environmental areas, such as landfill sites, river beds and sewage sludge. Direct chemical treatment of PCBs in such contaminated sites is often not feasible since the resulting treated solids are difficult to process further and recycle.

As shown by Colaruotolo et al., U.S. Pat. No. 4,447,570, an alternate procedure can be used for treating halogenated organic waste by effecting the removal of halogenated aromatics from the contaminated organic waste by microbial degradation. As taught by Colaruotolo et al., microorganisms have been identified having the capability of efficiently utilizing various aromatic organic chemicals as carbon sources for growth. In addition, microorganisms also have been isolated from the environment that are capable of growing in the presence of chlorinated aromatic compounds. Experience has shown, however, that PCBs found in weathered environmental soil samples, often contain five or more chemically combined chlorine atoms per molecule, indicating that such polychlorinated biphenyls generally resist biodegradation.

It has been further found that not only does the total number of chemically combined chlorine atoms per biphenyl nucleus influence the manner by which PCBs resist biodegradation, but the location of chlorine atoms substitution on the biphenyl nucleus is also an important factor. For example, the positions of chlorine substitution on a biphenyl nucleus is shown as follows:

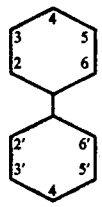

(1)

It has been found that PCB congeners having all 2,3 positions blocked by chlorine atoms often require a 3,4-dioxygenase, while those having all 3,4 positions blocked often require a 2,3-dioxygenase for aerobic bacterial degradation. Theoretically, PCBs having no vicinal unchlorinated carbon atoms would not be degradable by a dioxygenase.

It would be desirable, therefore, to provide aerobic bacteria capable of degrading a broad spectrum of PCBs having more than five chlorine atoms per biphenyl nucleus, including those having either 2,3 positions blocked, 3,4 positions blocked, those having all of these positions blocked, or no 2,3 or 3,4 positions available, or PCB congeners having no vicinal unchlorinated carbon atoms.

The present invention is based on the discovery that a particular strain of Pseudomonas, having the identifying characteristics of Pseudomonas putida NRRL B-18064 can be used to degrade PCB congeners having no vicinal unchlorinated carbon atoms, having only 2,3 positions unchlorinated, having only 3,4 positions unchlorinated, and having both 2,3 and 3,4 positions unchlorinated. The aforementioned Pseudomonas strain, or "LB400", was isolated from a soil sample contaminated with Aroclor 1242 and obtained from a dump site. Another unexpected feature of the present invention is the enrichment procedure employed leading to the selection of LB400, utilizing as a sole carbon source, a mixture of biphenyl and monochlorobiphenyl-containing PCB having an average of at least about 15% of chemically combined chlorine by weight. In addition, LB400 has been found to provide metabolites comprising 3,4- and 2,3-dihydroxybiphenyls and epoxy-substituted biphenyls.

STATEMENT OF THE INVENTION

There is provided by the present invention a biologically pure culture of microorganism of the genus and species Pseudomonas putida having genetic material promoting utilization as a sole carbon source, a mixture of biphenyl and monochlorobiphenyl-containing PCB having an average of at least about 15% of chemically combined chlorine by weight.

There is further provided by the present invention, an enrichment procedure for isolating microorganisms capable of biodegrading PCBs free of vicinal hydrogens and having an average of at least about 15% by weight of chemically combined chlorine atoms, which comprises (1) agitating under aerobic conditions for a period of at least 24 hours and at a temperature of from about 15° C. to 37° C. a mixture comprising
   (a) a PCB contaminated environmental sample,
   (b) mineral salts medium,
   (c) biphenyl.
   (d) a monochlorobiphenyl-containing PCB mixture having at least 15% by weight chlorine, (2) making several serial dilutions of the mixture of (1) at concentrations of $10^{-2}$ to $10^{-6}$, (3) plating aliquots of the dilutions on solid medium containing biphenyl as sole carbon and energy source, and (4) selecting clones.

Some of the congeners which can be biodegraded under aerobic conditions utilizing LB400 in accordance with the practice of the present invention are shown, with reference to Formula 1, by the following biphenyls:

| | |
|---|---|
| 2,4'- | 2,3,2',5'- |
| 2,2'- | 2,5,2',5'- |
| 2,3'- | 2,4,5,2',5'- |
| 2,5,2'- | 4,4'- |
| 2,5,4'- | 2,4,4'- |
| 2,3,2',3'- | 2,4,2',4'- |
| 2,4,3',4'- | 2,5,3',4'- |
| 3,4,3',4'- | 2,4,5,3',5'- |
| 2,3,4,2',5'- | 2,4,5,2',4',5'- |
| 2,4,5,2',3'- | 2,5,2',6'- |
| 2,4,6,2',5'- | 2,3,6,2',3',6'- |

-continued 2,4,6,3',4'-

Among the metabolites generated in accordance with the practice of the method of the present invention there are included dihydroxybiphenyls and epoxy-substituted biphenyls. Some of the dihydroxybiphenyls which can be made in accordance with the practice of the present invention are, for example,

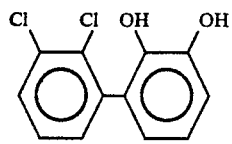

2,3-dihydroxy-
2',3'-dichlorobiphenyl

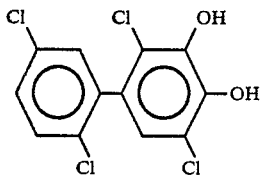

3,4-dihydroxy-
2,5,2',5'-tetrachloro-
biphenyl

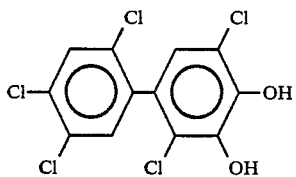

3,4-dihydroxy-
2,5,2',4',5'-pentachloro-
biphenyl

Some of the epoxy-biphenyls which can be made in accordance with the practice of the present invention are, for example,

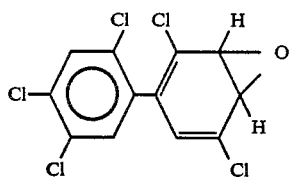

3,4-epoxide of
2,4,5,2',5'-pentachloro-
biphenyl

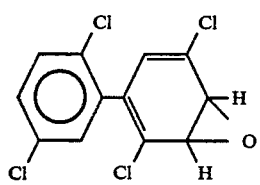

3,4-epoxide of
2,5,2',5'-tetrachloro-
biphenyl

PCBs have been used widely in industrial applications because of their thermal stability, excellent dielectric (electrically insulating) properties, and resistance to oxidation, acids, bases, and other chemical agents Complex mixtures of PCBs have been marketed under the tradename Aroclor (Monsanto Company, USA). The PCBs have been released into the environment for many years and are a worldwide contaminant. They are lipophilic and sorb strongly to the lipids and fats of animals, including fish, mussels, and birds. PCBs also undergo biological magnification in such common aquatic invertebrates as daphnids, mosquito larvae, stoneflies, and crayfish. The concentration of PCBs in the invertebrates can be as high as 27,500 times that in water. As these invertebrates are subsequently eaten by fish and birds, bioaccumulation occurs at all levels of the food chain.

As used hereinafter, the term "Aroclor 12XX" indicates a commercial mixture of chlorinated biphenyls, where the digits indicated by XX correspond to the weight mixture percent chlorine. Accordingly, Aroclor 1242 is 42% chlorine by weight, averages 3 chlorines per molecule, and contains some molecules having five or more chlorines per molecule.

A culture of the bacterium *Pseudomonas putida* or LB400 is on deposit with the U.S. department of Agriculture as NRRL B-18064. A progeny of the subject microorganism will be provided by the assignee of this application under the conditions imposed by 37 CFR 1.14 and 35 USC 122 in the event that the Commissioner of Patents and Trademarks determines that an individual is entitled to same.

Upon issuance of the subject application as a patent, subculture of this strain can be obtained from the permanent collection of the Agricultural Research Culture Collection (NRRL) at the Northern Regional Research Center, U.S. Department of Agriculture, Peoria, Ill., U.S.A.

The taxonomic identification of LB400 was made and it was found to be *Pseudomonas putida* having the following physiological and biochemical characteristics:

| | |
|---|---|
| gram stain | − |
| motility | + |
| cytochrome oxidase | + |
| ONPG hydrolysis | − |
| H$_2$S production | − |
| glucose fermentation | − |
| pyocin production | − |
| N$_2$ gas production | − |
| growth at 42° C. | − |
| glucose utilization | + |
| xylose utilization | + |
| mannitol utilization | + |
| lactose utilization | − |
| maltose utilization | − |
| acetamide utilization | − |
| esculin utilization | − |
| indole production | − |
| growth on MacConkey agar | + |
| cetrimide resistance | + |
| fluorescein production | − |
| urease | +/− |
| DNAse | − |
| gelatin hydrolysis | − |
| obligatedly aerobic rod ∼0.8 by 2.0 μm | |

In practice of the invention, LB400 can be used to biodegrade halogenated organic waste, which hereinafter means contaminated soil from landfill sites, river beds, leachates therefrom, and aqueous surfactant solutions resulting from washing the aforementioned organic waste to transfer the PCBs to the aqueous surfactant solution. One method of treating the organic waste is by inoculating or reintroducing LB400 to the contaminated environment. For example, the bacteria can be injected with nutrient media and oxygen into the landfill site. Biodegradation can be monitored to determine the effectiveness of the treatment.

Surfactants which can be used in the practice of the present invention to wash PCB contaminated organic waste are, for example, Surco 233, a sodium salt of an alkylene benzene sulfonate made by the ONYX Chemical Co. of Jersey City, N.J.

In order that those skilled in the art will be better able to practice the present invention, the following examples are given by way of illustration and not by way of limitation. All parts are by weight.

EXAMPLE 1

A mixed bacterial culture was obtained from a PCB-contaminated soil collected from a landfill in Moreau, N.Y. About 0.5 g of the soil was incubated in about 20 ml of PAS medium containing 0.01% yeast extract, 0.05% glucose, 0.2 ml biphenyl, and 100 ul of Aroclor 1221. The phosphate buffered minimal salts medium was then incubated aerobically for 96 hours at 30° C. with shaking. After the sediment was allowed to settle, aliquots of the liquid culture were removed, and serial 10-fold dilutions were made in sterile saline.

All colonies which differed in colonial morphology were picked. Colonies judged to be pure on the basis of both macroscopic examination and microscopic examination after gram staining were inoculated into biphenyl-containing phosphate-buffered minimal salts medium. Pure cultures capable of utilizing biphenyl as a sole carbon and energy source were plated out onto Luria agar. In each case, a single colony of the pure culture was selected. Part of the colony was used to inoculate biphenyl/phosphate-buffered broth to establish a stock culture. The remainder of the colony was tested for a gram reaction and characterized using the N/F system (Flow Laboratories, Inc.) Different colonies were isolated and characterized on the basis of the gram reaction, motility, morphology and the 17 parameters of the N/F system. The purity of each isolate was confirmed by gram stain and macroscopic examination of colonies. LB400 was identified as a strain of *Pseudomonas putida*, an aerobic bacterium commonly found in soil, mud, and water.

LB400 cells were grown to an optical density of 1.0 at 600 nm, then washed twice with a 50 mM solution of sodium phosphate buffer (pH 7.5). The cells were resuspended in the buffer and separated into 1 μl aliquots. There was added to each LB400 aliquot 10 μl of a stock solution (in acetone) of a synthetic mixture of PCB congeners containing a non-biodegradable internal standard or 10 μl of a stock solution (in acetone) of Aroclor 1248. When using the synthetic PCB mixtures, the final concentration of each PCB congener was 5 micromoles/liter. When using Aroclor 1248, the final PCB concentration in each sample was 10 ppm. The mixtures were then incubated in a gyratory incubator for 48 hours at 30° C. under sealed conditions. The cells were then killed by the addition of perchloric acid to a final concentration of 0.7%. Controls were prepared by killing the bacteria prior to the addition of PCBs by heating at 70° C. for 20 minutes or by adding $HgCl_2$ to a final concentration of 1.0 mM.

The entire contents of each vial were extracted in 4 volumes of ether. During extraction the samples were shaken vigorously for 20–30 minutes in a horizontal position on a reciprocating platform shaker. The phases separated rapidly without centrifugation. The samples containing the synthetic PCB mixtures were then analyzed isothermally at 190° C. on a Varian Model 6000 GC equipped with an automatic sampler, an electron capture detector and a glass column packed with 1.5% SP2250/1.95% SP2401 on 100/120 Supelcoport. Nitrogen was used as a carrier ending at a flow rate of 60 ml per minute. The samples containing Aroclor 1248 were analyzed on a Varian Vista GC 4600 equipped with an electron capture detector and splitter-injector, both operated at 300° C., and a fused silica capillary column coated with a 0.25 μM bonded liquid phase of Durabond-1. The carrier gas and makeup gas were helium (30 cm/s) and nitrogen (25 ml/min), respectively. Samples were chromatographed by using a temperature program which was held at 40° C. for 2 min., then raised to 80° C. at 10° C./min, then to 225° C. at 6° C./min, and held at 225° C. for 10 min. Injections (1 μl) were done by the splitless technique with a vent time of 0.9 min.

EXAMPLE 2

The procedure of Example 1 was repeated, except that environmental samples were enriched in media containing biphenyl alone, as well as a mixture of biphenyl and chlorobiphenyls as sole sources of carbon and energy. A 96-hour incubation period was utilized in both instances. Five pure cultures of bacteria isolated from the medium containing biphenyl alone and five pure cultures of bacteria isolated from the media containing biphenyl and Aroclor 1221 were analyzed for their ability to degrade PCBs.

PCB congener mixtures were prepared which included 10 PCBs with an internal standard [1B] and nine PCBs and an internal standard [2B]. The following table shows the composition of the PCB congener mixtures:

| Congener mix 1B | Congener mix 2B |
| --- | --- |
| 2,4' | 2,2' |
| 4,4' | 2,3 |
| 2,4,4' | 2,5,2' |
| 2,5,2',5' | 2,5,4' |
| 2,3,2',5' | 2,4,2',4' |
| 2,4,6,2',4'* | 2,4,6,2',4'* |
| 2,3,2',3' | 2,5,3',4' |
| 2,4,3',4' | 2,4,5,2',5' |
| 2,4,5,2',3' | 2,3,4,2',5' |
| 3,4,3',4' | 2,4,5,2',4',5' |
| 2,4,5,2',4',5' | |

*Non-degradable internal standard

Cells were grown, harvested by centrifugation, and washed twice in one half volume each time of sterile 50 mM sodium phosphate buffer (pH 7.5). Biphenyl crystals were removed by carefully pipeting the cell suspension away from the biphenyl, which had settled to the bottom. PCBs were usually added to a final concentration of one part per million of each cogener. Killed-cell controls were prepared by adding 20 μl of a 50 mM stock solution of $HgCl_2$ (final concentration of $HgCl_2$ was 1.0 mM) to a standard reaction vessel and incubating for 15 minutes before the addition of PCBs. Controls were also prepared at time zero by adding 10 μl of concentrated perchloric acid to each reaction vessel immediately following the addition of PCBs. All reaction vessels were incubated in the dark on a rotary shaker at 30° C. Reactions were stopped by the addition of 10 μl of perchloric acid.

Analysis of the results of the degradation of the described PCB mixtures by five bacterial strains obtained by enrichment with biphenyl alone and five bacterial strains obtained by enrichment with biphenyl and a PCB mixture containing monochlorbiphenyls and having at least 15% by weight of chlorine showed that the organisms obtained by enrichment with biphenyl and PCBs degraded an average of 12.5 out of the 19 PCB congeners to a degree of at least 50% by weight while the organisms obtained by enrichment on biphenyl alone degraded an average of only five of the 19 PCB congeners to a degree of at least 50% by weight.

It was further found that the particular organism of Example 1, referred to as LB400, degraded 19 out of the 19 PCB congeners, to at least about 50% by weight.

The same procedure as shown above was repeated except that the enrichment period was extended from four days to about 60 days and the cultures were transferred to fresh media (of the same composition as the original media) after 30 days by inoculating the fresh media with 5% (vol/vol) of the 30 day old cultures.

It was found that the ability of the organisms obtained by enrichment on biphenyl and the organisms obtained by enrichment on a mixture of biphenyl and PCBs containing monochlorobiphenyls and at least 15% by weight of chlorine to degrade the bulk mixture of 19 PCB congeners dropped significantly after the 60-day enrichment period. For example, the organisms obtained by enrichment strictly on biphenyl were able to degrade on the average only about 3 of the 19 congeners, whereas the organisms obtained by enrichment on a mixture of biphenyl and PCBs degraded the 19 congeners to an average of only about 5.3 of the 19.

The above data demonstrate that the enrichment procedure of the present invention utilizing a mixture of biphenyl and PCBs containing monochlorobiphenyls results in the acquisition of bacterial strains which have superior PCB-degradative competence as compared to those strains obtained with the enrichment procedure of the prior art utilizing only biphenyl as the sole source of carbon and energy. In addition, the incubation period of 96 hours vs. 60 days shows that the 96-hour incubation period is preferable over the 60-day incubation period.

EXAMPLE 3

The frozen stock culture of LB400, as prepared in Example 1, was used to inoculate Luria broth. Cells were allowed to grow overnight at 30° C with agitation and then washed twice with 50 mM sodium phosphate buffer having a pH of 7.5 and then resuspended in the same buffer. There was then added 1/100 volume of 2,4,5,2', 5'-chlorobiphenyl from an acetone stock solution to the cell suspension. The mixture was incubated at 30° C. with agitation for 12 hours. Metabolites were extracted with acid/ether and purified by HPLC using a reverse phase C-18 column and a water-acetonitrile gradient. Structural characterization by GC, GC-MS and MS showed the formation of 3,4-dihydroxy-2,5,2',4',5'-pentachlorobiphenyl.

The same procedure was repeated except that 2,3-dichlorobiphenyl was used as the congener. There was then obtained 2,3-dihydroxy-2',3'-dichlorobiphenyl.

EXAMPLE 4

In accordance with the procedure of Example 3, resting cells were prepared and 2,4,5,2',5'-pentachlorobiphenyl was added to the mixture as the substrate. Following incubation, metabolites were extracted in neutral ether and purified by HPLC as described in Example 3. Structural analysis showed the presence of the 3,4-epoxide of 2,4,5,2',5'-pentachlorobiphenyl, which was further confirmed by comparison with an authentic standard of a PCB epoxide.

EXAMPLE 5

The procedure of Example 2 was repeated with respect to the evaluation of the organism designated LB400 and obtained in accordance with the enrichment procedure of Example 1 utilizing biphenyl, monochlorobiphenyls and other PCBs. However, in place of the mixture of congeners evaluated in accordance with Example 2, PCBs bound to soil were evaluated. LB400 was grown in the mineral salts medium with biphenyl as the sole carbon source, then harvested, washed, and resuspended in buffer to approximately $10^9$ cell per ml. The washed cells were then incubated with one of several PCB/soil formulations. In one study, 50 ppm of Aroclor 1242 was added to clean, PCB-free soil. In another study, 500 ppm of Aroclor 1242 was used to treat clean soil. A further soil sample was prepared utilizing 50 ppm of Aroclor 1254 on clean soil. An environmental sample containing 525 ppm of PCB was also evaluated.

After approximately 2–3 days incubation it was found that 95% of the Aroclor 1242 employed at a concentration of 50 ppm on clean soil was degraded. 85% of the Aroclor 1242 at a concentration of 500 ppm was degraded, while 65% of the Aroclor 1254, and 50% of the PCB in the environmental sample was degraded.

Although the above examples are directed to only a few of the very many variables which can be used in the practice of the present invention, it should be understood that the method of the present invention involves the use of LB400 to degrade a much broader variety of PCBs as well as PCBs on other substrates and at other temperatures and conditions as shown in the description preceding these examples.

What I claim as new and desire to secure by Letters Patent of the United States is:

1. An enrichment procedure for isolating microorganisms capable of biodegrading PCB cogeners which comprises,
   (1) cogeners selected from the class of cogeners free of vicinal hydrogen atoms, cogeners having unchlorinated 2,3 positions, cogeners having unchlorinated 3,4 positions, and cogeners unchlorinated in both 2,3 and 3,4 positions,
   (2) agitating under aerobic conditions for a period of at least 24 hours and at a temperature of from about 15° C. to 37° C. a mixture comprising
      (a) a PCB contaminated environmental sample
      (b) mineral salts medium,
      (c) biphenyl, and
      (d) a monochlorobiphenyl-containing PCB mixture having at least 15% by weight chlorine,
   (3) making several serial dilutions of the mixture of (2) at concentrations of $10^{-2}$ to $10^{-6}$,
   (4) plating aliquots of the dilutions on solid medium containing biphenyl as sole carbon and energy source, and
   (5) selecting clones.

2. A process for making 2,3-dihydroxy chlorinated biphenyl comprising incubating under aerobic conditions, a mixture comprising *Pseudomonas putida* NRLL B-18064 and a PCB congener having an unchlorinated 2,3 position or equivalent 5,6 position and recovering a 2,3-dihydroxy chlorinated biphenyl from the resulting mixture.

3. A process in accordance with claim 2, where the PCB congener is 2,3-dischlorobiphenyl.

4. A process for making 3,4-dihydroxy chlorinated biphenyl comprising incubating under aerobic conditions a mixture comprising *Pseudomonas putida* NRLL B-18064 and PCB congener having an unchlorinated 3,4 position and recovering a 3,4-dihydroxy chlorinated biphenyl from the resulting mixture.

5. A process in accordance with claim 4, where the PCB congener is 2,4,5,2',5'-pentachlorobiphenyl.

6. A process for making a 3,4-epoxide of a chlorinated biphenyl which comprises incubating under aerobic conditions a PCB congener having an unchlorinated 3,4 position with *Pseudomonas putida* NRRL B-18064 and recovering a 3,4-epoxy- chlorinated biphenyl from the resulting mixture.

7. A process in accordance with claim 6 where the PCB congener is 2,4,5,2',5'-pentachlorobiphenyl.

8. A biodegradation process comprising incubating under aerobic conditions, a surfactant solution of PCBs in the presence of a biologically pure culture of a strain of *Pseudomonas putida*.

9. A biodegradation process comprising incubating under aerobic conditions, soil-bound PCBs in the presence of a biologically pure culture of a strain of *Pseudomonas putida*.

* * * * *